(12) United States Patent
Baynham et al.

(10) Patent No.: US 8,340,764 B2
(45) Date of Patent: *Dec. 25, 2012

(54) METHOD AND APPARATUS FOR CARDIAC PROTECTION PACING

(75) Inventors: Tamara Colette Baynham, Piscataway, NJ (US); Yi Zhang, Plymouth, MN (US); Joseph M. Pastore, Concord, OH (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/029,631

(22) Filed: Feb. 17, 2011

(65) Prior Publication Data

US 2011/0144709 A1 Jun. 16, 2011

Related U.S. Application Data

(62) Division of application No. 11/129,050, filed on May 13, 2005, now Pat. No. 7,917,210.

(51) Int. Cl.
A61B 8/14 (2006.01)
(52) U.S. Cl. ............... 607/9; 600/508; 600/439
(58) Field of Classification Search .............. 607/9
See application file for complete search history.

(56) References Cited

U.S. PATENT DOCUMENTS

| | | | |
|---|---|---|---|
| 4,834,710 A | 5/1989 | Fleck | |
| 5,007,427 A | 4/1991 | Suzuki et al. | |
| 5,072,458 A | 12/1991 | Suzuki | |
| 5,085,215 A | 2/1992 | Nappholz et al. | |
| 5,111,818 A | 5/1992 | Suzuki et al. | |
| 5,135,004 A | 8/1992 | Adams et al. | |
| 5,170,802 A | 12/1992 | Mehra | |
| 5,184,615 A | 2/1993 | Nappholz et al. | |
| 5,199,428 A | 4/1993 | Obel et al. | |
| 5,203,326 A | 4/1993 | Collins | |
| 5,282,840 A | 2/1994 | Hudrlik | |
| 5,313,953 A | 5/1994 | Yomtov et al. | |
| 5,334,221 A | 8/1994 | Bardy | |
| 5,447,529 A | 9/1995 | Marchlinski et al. | |
| 5,484,419 A | 1/1996 | Fleck | |
| 5,531,768 A | 7/1996 | Alferness | |

(Continued)

FOREIGN PATENT DOCUMENTS

CA 2459408 A1 3/2003

(Continued)

OTHER PUBLICATIONS

"U.S. Appl. No. 11/030,575, Non-Final Office Action mailed Jul. 26, 2006", 10 pgs.

(Continued)

*Primary Examiner* — Carl H. Layno
*Assistant Examiner* — Jon-Eric C. Morales
(74) *Attorney, Agent, or Firm* — Schwegman Lundberg & Woessner, P.A.

(57) ABSTRACT

A pacing system delivers cardiac protection pacing to protect the heart from injuries associated with ischemic events. The pacing system detects an ischemic event and, in response, initiates one or more cardiac protection pacing sequences each including alternative pacing and non-pacing periods. In one embodiment, the pacing system initiates cardiac protection pacing sequences including at least one postconditioning sequence to protect the heart from a detected ischemic event and a plurality prophylactic preconditioning sequences to protect the heart from probable future ischemic events.

20 Claims, 5 Drawing Sheets

U.S. PATENT DOCUMENTS

| | | | |
|---|---|---|---|
| 5,531,779 A | 7/1996 | Dahl et al. | |
| 5,800,466 A | 9/1998 | Routh et al. | |
| 5,919,209 A | 7/1999 | Schouten | |
| 5,954,761 A | 9/1999 | Machek et al. | |
| 6,021,350 A | 2/2000 | Mathson | |
| 6,108,577 A | 8/2000 | Benser | |
| 6,151,525 A | 11/2000 | Soykan et al. | |
| 6,256,538 B1 | 7/2001 | Ekwall | |
| 6,272,379 B1 | 8/2001 | Fischell et al. | |
| 6,278,894 B1 | 8/2001 | Salo et al. | |
| 6,285,907 B1 | 9/2001 | Kramer et al. | |
| 6,314,323 B1 | 11/2001 | Ekwall | |
| 6,368,284 B1 | 4/2002 | Bardy | |
| 6,477,402 B1 | 11/2002 | Lynch et al. | |
| 6,477,406 B1 | 11/2002 | Turcott | |
| 6,501,983 B1 | 12/2002 | Natarajan et al. | |
| 6,569,145 B1 | 5/2003 | Shmulewitz et al. | |
| 6,584,362 B1 | 6/2003 | Scheiner et al. | |
| 6,604,000 B2 | 8/2003 | Lu | |
| 6,628,988 B2 | 9/2003 | Kramer et al. | |
| 6,666,826 B2 | 12/2003 | Salo et al. | |
| 6,711,436 B1 | 3/2004 | Duhaylongsod | |
| 6,813,516 B2 | 11/2004 | Ujhelyi et al. | |
| 6,827,690 B2 | 12/2004 | Bardy | |
| 6,842,642 B2 | 1/2005 | Vanhout | |
| 6,845,267 B2 | 1/2005 | Harrison et al. | |
| 6,865,420 B1 | 3/2005 | Kroll | |
| 6,913,577 B2 | 7/2005 | Bardy | |
| 6,937,899 B2 * | 8/2005 | Sheldon et al. | 607/18 |
| 6,950,701 B2 | 9/2005 | Begemann et al. | |
| 6,957,104 B2 | 10/2005 | Wagner | |
| 6,965,797 B2 | 11/2005 | Pastore et al. | |
| 6,973,349 B2 | 12/2005 | Salo | |
| 7,003,350 B2 | 2/2006 | Denker et al. | |
| 7,010,345 B2 | 3/2006 | Hill et al. | |
| 7,039,462 B2 | 5/2006 | Pastore et al. | |
| 7,043,305 B2 | 5/2006 | Kenknight et al. | |
| 7,062,325 B1 | 6/2006 | Krig et al. | |
| 7,069,070 B2 | 6/2006 | Carlson et al. | |
| 7,072,711 B2 | 7/2006 | Girouard et al. | |
| 7,082,336 B2 | 7/2006 | Ransbury et al. | |
| 7,171,258 B2 | 1/2007 | Goode | |
| 7,215,997 B2 | 5/2007 | Yu et al. | |
| 7,236,821 B2 | 6/2007 | Cates et al. | |
| 7,277,761 B2 | 10/2007 | Shelchuk | |
| 7,295,874 B2 | 11/2007 | Prinzen et al. | |
| 7,299,087 B2 | 11/2007 | Bardy | |
| 7,340,303 B2 | 3/2008 | Zhu | |
| 7,364,547 B2 | 4/2008 | Stahmann et al. | |
| 7,366,568 B2 | 4/2008 | Pastore et al. | |
| 7,437,191 B2 | 10/2008 | Pastore et al. | |
| 7,460,906 B2 | 12/2008 | Libbus | |
| 7,479,112 B2 | 1/2009 | Sweeney et al. | |
| 7,486,991 B2 | 2/2009 | Libbus et al. | |
| 7,493,162 B2 | 2/2009 | Girouard et al. | |
| 7,582,061 B2 | 9/2009 | Li et al. | |
| 7,668,594 B2 | 2/2010 | Brockway et al. | |
| 7,736,319 B2 | 6/2010 | Patangay et al. | |
| 7,780,606 B2 | 8/2010 | Carlson et al. | |
| 7,885,710 B2 | 2/2011 | Sih et al. | |
| 7,894,896 B2 | 2/2011 | Baynham et al. | |
| 7,917,210 B2 * | 3/2011 | Baynham et al. | 607/9 |
| 7,922,669 B2 | 4/2011 | Zhang et al. | |
| 7,938,781 B2 | 5/2011 | Carlson et al. | |
| 7,962,208 B2 | 6/2011 | Shuros et al. | |
| 7,979,123 B2 | 7/2011 | Prinzen et al. | |
| 8,000,780 B2 | 8/2011 | Wariar et al. | |
| 8,034,000 B2 | 10/2011 | Zhang et al. | |
| 8,214,040 B2 | 7/2012 | Pastore et al. | |
| 2002/0042632 A1 | 4/2002 | Iaizzo et al. | |
| 2002/0072777 A1 * | 6/2002 | Lu | 607/17 |
| 2002/0082660 A1 | 6/2002 | Stahmann et al. | |
| 2002/0143369 A1 | 10/2002 | Hill et al. | |
| 2003/0004549 A1 | 1/2003 | Hill et al. | |
| 2003/0009189 A1 | 1/2003 | Gilson et al. | |
| 2003/0045908 A1 | 3/2003 | Condie et al. | |
| 2003/0055461 A1 | 3/2003 | Girouard et al. | |
| 2003/0060854 A1 | 3/2003 | Zhu | |
| 2003/0120313 A1 | 6/2003 | Begemann et al. | |
| 2003/0120315 A1 | 6/2003 | Spinelli et al. | |
| 2003/0139778 A1 | 7/2003 | Fischell et al. | |
| 2003/0158492 A1 | 8/2003 | Sheldon et al. | |
| 2003/0158583 A1 | 8/2003 | Burnett et al. | |
| 2003/0158584 A1 | 8/2003 | Cates et al. | |
| 2003/0204206 A1 | 10/2003 | Padua et al. | |
| 2003/0204231 A1 | 10/2003 | Hine et al. | |
| 2003/0233130 A1 | 12/2003 | Padmanabhan et al. | |
| 2003/0233132 A1 | 12/2003 | Pastore et al. | |
| 2004/0015081 A1 * | 1/2004 | Kramer et al. | 600/439 |
| 2004/0038947 A1 | 2/2004 | Wink et al. | |
| 2004/0049235 A1 | 3/2004 | Deno et al. | |
| 2004/0088017 A1 * | 5/2004 | Sharma et al. | 607/25 |
| 2004/0106960 A1 | 6/2004 | Siejko et al. | |
| 2004/0127792 A1 | 7/2004 | Siejko et al. | |
| 2004/0133247 A1 | 7/2004 | Stahmann et al. | |
| 2004/0255956 A1 | 12/2004 | Vinten-Johansen et al. | |
| 2005/0004476 A1 | 1/2005 | Payvar et al. | |
| 2005/0038345 A1 | 2/2005 | Gorgenberg et al. | |
| 2005/0043675 A1 | 2/2005 | Pastore et al. | |
| 2005/0075673 A1 | 4/2005 | Warkentin et al. | |
| 2005/0137483 A1 | 6/2005 | Fischell et al. | |
| 2005/0137631 A1 | 6/2005 | Yu et al. | |
| 2005/0143779 A1 | 6/2005 | Libbus | |
| 2005/0143780 A1 | 6/2005 | Henry et al. | |
| 2005/0149129 A1 | 7/2005 | Libbus et al. | |
| 2005/0171589 A1 | 8/2005 | Lau et al. | |
| 2005/0197674 A1 | 9/2005 | McCabe et al. | |
| 2005/0261741 A1 | 11/2005 | Libbus et al. | |
| 2005/0283195 A1 | 12/2005 | Pastore et al. | |
| 2005/0288721 A1 | 12/2005 | Girouard et al. | |
| 2006/0020294 A1 | 1/2006 | Brockway et al. | |
| 2006/0030892 A1 | 2/2006 | Kadhiresan et al. | |
| 2006/0116593 A1 | 6/2006 | Zhang et al. | |
| 2006/0149326 A1 | 7/2006 | Prinzen et al. | |
| 2006/0206158 A1 | 9/2006 | Wu et al. | |
| 2006/0241357 A1 | 10/2006 | Chirife | |
| 2006/0241704 A1 | 10/2006 | Shuros et al. | |
| 2006/0247686 A1 | 11/2006 | Girouard et al. | |
| 2006/0247700 A1 * | 11/2006 | Jackson | 607/9 |
| 2006/0253156 A1 | 11/2006 | Pastore et al. | |
| 2006/0259088 A1 | 11/2006 | Pastore et al. | |
| 2006/0282000 A1 | 12/2006 | Zhang et al. | |
| 2006/0287684 A1 | 12/2006 | Baynham et al. | |
| 2007/0021789 A1 | 1/2007 | Pastore et al. | |
| 2007/0043393 A1 | 2/2007 | Brockway et al. | |
| 2007/0049835 A1 | 3/2007 | Goode | |
| 2007/0054871 A1 | 3/2007 | Pastore et al. | |
| 2007/0150005 A1 | 6/2007 | Sih et al. | |
| 2007/0150015 A1 | 6/2007 | Zhang et al. | |
| 2007/0162081 A1 | 7/2007 | Yu et al. | |
| 2007/0179392 A1 | 8/2007 | Zhang | |
| 2007/0203524 A1 | 8/2007 | Sheldon et al. | |
| 2007/0239218 A1 | 10/2007 | Carlson et al. | |
| 2007/0282380 A1 | 12/2007 | Brooke et al. | |
| 2007/0299356 A1 | 12/2007 | Wariar et al. | |
| 2008/0027495 A1 | 1/2008 | Prinzen et al. | |
| 2008/0058661 A1 | 3/2008 | Bardy | |
| 2008/0058881 A1 | 3/2008 | Wagner et al. | |
| 2008/0071315 A1 | 3/2008 | Baynham et al. | |
| 2008/0081354 A1 | 4/2008 | Qu et al. | |
| 2008/0082135 A1 | 4/2008 | Arcot et al. | |
| 2008/0091138 A1 | 4/2008 | Pastore et al. | |
| 2008/0132972 A1 | 6/2008 | Shuros et al. | |
| 2008/0140141 A1 | 6/2008 | Ben-David et al. | |
| 2008/0177156 A1 | 7/2008 | Zhang et al. | |
| 2008/0177191 A1 | 7/2008 | Patangay et al. | |
| 2008/0177194 A1 | 7/2008 | Zhang et al. | |
| 2008/0221636 A1 | 9/2008 | Pastore et al. | |
| 2009/0025459 A1 | 1/2009 | Zhang et al. | |
| 2009/0048641 A1 | 2/2009 | Libbus | |
| 2009/0082781 A1 | 3/2009 | Tran et al. | |
| 2009/0124916 A1 | 5/2009 | Sweeney et al. | |
| 2009/0192560 A1 | 7/2009 | Arcot-Krishnamurthy et al. | |
| 2009/0287106 A1 | 11/2009 | Zhang et al. | |
| 2010/0121391 A1 | 5/2010 | Brockway et al. | |
| 2010/0130913 A1 | 5/2010 | Baynham et al. | |
| 2010/0249863 A1 | 9/2010 | Carlson et al. | |

| 2010/0274306 | A1 | 10/2010 | Pastore et al. |
| 2011/0077701 | A1 | 3/2011 | Sih et al. |
| 2011/0137363 | A1 | 6/2011 | Baynham et al. |
| 2011/0230928 | A1 | 9/2011 | Shuros et al. |
| 2012/0004565 | A1 | 1/2012 | Zhang et al. |

FOREIGN PATENT DOCUMENTS

| EP | 1690566 | A1 | 8/2006 |
| JP | 4221577 | | 8/1992 |
| JP | 7504597 | A | 5/1995 |
| JP | 2001520547 | A | 10/2001 |
| JP | 2002514478 | A | 5/2002 |
| JP | 2004533297 | A | 11/2004 |
| JP | 2005501617 | A | 1/2005 |
| JP | 2005063332 | A | 3/2005 |
| JP | 2005177458 | A1 | 7/2005 |
| JP | 2008539983 | A | 11/2008 |
| JP | 4995191 | A | 5/2012 |
| WO | WO-9400192 | | 1/1994 |
| WO | WO-9518649 | A1 | 7/1995 |
| WO | WO-9958191 | A1 | 11/1999 |
| WO | WO-0115609 | A1 | 3/2001 |
| WO | WO-2004058326 | A2 | 7/2004 |
| WO | WO-2005042083 | A2 | 5/2005 |
| WO | WO-2006074189 | A1 | 7/2006 |
| WO | WO-2006115693 | A2 | 11/2006 |
| WO | WO-2006115693 | A3 | 11/2006 |
| WO | WO-2006121842 | A2 | 11/2006 |
| WO | WO-2006124636 | A2 | 11/2006 |
| WO | WO-2006124636 | A3 | 11/2006 |
| WO | WO-2006124729 | A2 | 11/2006 |
| WO | WO-2006124729 | A3 | 11/2006 |
| WO | WO-2007133962 | A2 | 11/2007 |
| WO | WO-2007133962 | A3 | 11/2007 |

OTHER PUBLICATIONS

"U.S. Appl. No. 11/030,575, Notice of Allowance mailed Jan. 17, 2007", 7 pgs.

"U.S. Appl. No. 11/030,575, Notice of Allowance mailed Jun. 7, 2007", 7 pgs.

"U.S. Appl. No. 11/030,575, Response filed Oct. 26, 2006 to Non Final Office Action mailed Jul. 26, 2006", 8 pgs.

"U.S. Appl. No. 11/113,828, Non-Final Office Action mailed Mar. 5, 2008", 8 pgs.

"U.S. Appl. No. 11/113,828, Advisory Action mailed Feb. 2, 2010", 3 pgs.

"U.S. Appl. No. 11/113,828, Examiner Interview Summary received Feb. 4, 2011", 1 pg.

"U.S. Appl. No. 11/113,828, Final Office Action mailed Jun. 29, 2009", 11 pgs.

"U.S. Appl. No. 11/113,828, Final Office Action mailed Sep. 17, 2008", 10 pgs.

"U.S. Appl. No. 11/113,828, Final Office Action mailed Nov. 24, 2009", 13 pgs.

"U.S. Appl. No. 11/113,828, Non-Final Office Action mailed Dec. 22, 2008", 10 pgs.

"U.S. Appl. No. 11/113,828, Notice of Allowance mailed Feb. 4, 2011", 7 pgs.

"U.S. Appl. No. 11/113,828, Notice of Allowance mailed Oct. 19, 2010", 4 pgs.

"U.S. Appl. No. 11/113,828, Response filed Jan. 25, 2010 to Final Office Action mailed Nov. 24, 2009", 8 pgs.

"U.S. Appl. No. 11/113,828, Response filed Jan. 28, 2008 to Restriction Requirement mailed Dec. 26, 2007", 7 pgs.

"U.S. Appl. No. 11/113,828, Response filed Mar. 23, 2009 to Non-Final Office Action mailed Dec. 22, 2008", 8 pgs.

"U.S. Appl. No. 11/113,828, Response filed Jun. 5, 2008 to Non-Final Office Action mailed Mar. 5, 2008", 8 pgs.

"U.S. Appl. No. 11/113,828, Response filed Oct. 29, 2009 to Final Office Action mailed Jun. 29, 2009", 9 pgs.

"U.S. Appl. No. 11/113,828, Response filed Nov. 17, 2008 to Final Office Action mailed Sep. 17, 2008", 11 pgs.

"U.S. Appl. No. 11/113,828, Restriction Requirement mailed Dec. 26, 2007", 8 pgs.

"U.S. Appl. No. 11/129,050, Advisory Action mailed Jul. 14, 2009", 3 pgs.

"U.S. Appl. No. 11/129,050, Advisory Action mailed Jul. 28, 2008", 3 pgs.

"U.S. Appl. No. 11/129,050, Examiner Interview Summary mailed Feb. 11, 2009", 2 pgs.

"U.S. Appl. No. 11/129,050, Final Office Action mailed Apr. 21, 2009", 10 pgs.

"U.S. Appl. No. 11/129,050, Final Office Action mailed May 12, 2008", 8 pgs.

"U.S. Appl. No. 11/129,050, Non-Final Office Action mailed Nov. 6, 2008", 7 pgs.

"U.S. Appl. No. 11/129,050, Non-Final Office Action mailed Nov. 26, 2007", 7 pgs.

"U.S. Appl. No. 11/129,050, Notice of Allowance mailed Apr. 1, 2010", 6 pgs.

"U.S. Appl. No. 11/129,050, Notice of Allowance mailed Jul. 16, 2010", 4 pgs.

"U.S. Appl. No. 11/129,050, Notice of Allowance mailed Aug. 24, 2009", 7 pgs.

"U.S. Appl. No. 11/129,050, Notice of Allowance mailed Nov. 1, 2010", 6 pgs.

"U.S. Appl. No. 11/129,050, Notice of Allowance mailed Dec. 2, 2009", 4 pgs.

"U.S. Appl. No. 11/129,050, Response filed Feb. 23, 2009 to Non-Final Office Action mailed Nov. 6, 2008", 13 pgs.

"U.S. Appl. No. 11/129,050, Response filed Feb. 26, 2008 to Non-Final Office Action mailed Nov. 26, 2007", 14 pgs.

"U.S. Appl. No. 11/129,050, Response filed Jun. 22, 2009 to Final Office Action mailed Apr. 21, 2009", 9 pgs.

"U.S. Appl. No. 11/129,050, Response filed Jul. 14, 2008 to Final Office Action mailed May 12, 2008", 13 pgs.

"U.S. Appl. No. 11/129,050, Response filed Sep. 28, 2007 to Restriction Requirement mailed Aug. 1, 2007", 11 pgs.

"U.S. Appl. No. 11/129,050, Restriction Requirement mailed Aug. 1, 2007", 6 pgs.

"U.S. Appl. No. 11/129,050, Supplemental Amendment and Response filed Sep. 12, 2008 to Final Office Action mailed May 12, 2008 and the Advisory Action mailed Jul. 28, 2008", 12 pgs.

"U.S. Appl. No. 11/129,058, Advisory Action mailed Oct. 17, 2007", 3 pgs.

"U.S. Appl. No. 11/129,058, Appeal Brief filed Jan. 8, 2008", 23 pgs.

"U.S. Appl. No. 11/129,058, Decision on Appeal mailed Nov. 4, 2009", 15 pgs.

"U.S. Appl. No. 11/129,058, Examiner's Answer to Appeal Brief mailed Jun. 18, 2008", 14 pgs.

"U.S. Appl. No. 11/129,058, Final Office Action mailed Jul. 9, 2007", 12 pgs.

"U.S. Appl. No. 11/129,058, Non-Final Office Action mailed Jan. 29, 2007", 11 pgs.

"U.S. Appl. No. 11/129,058, Office Communication mailed Jan. 15, 2010", 2 pgs.

"U.S. Appl. No. 11/129,058, Response filed Apr. 30, 2007 to Non Final Office Action mailed Jan. 29, 2007", 16 pgs.

"U.S. Appl. No. 11/129,058, Response filed Oct. 9, 2007 to Final Office Action mailed Jul. 9, 2007", 14 pgs.

"U.S. Appl. No. 11/382,568, Response filed Sep. 25, 2008 to Final Office Action mailed Jun. 25, 2008", 11 pgs.

"U.S. Appl. No. 11/382,568, Final Office Action mailed Jun. 25, 2008", 7 pgs.

"U.S. Appl. No. 11/382,849, Final Office Action mailed Jan. 28, 2010", 7 pgs.

"U.S. Appl. No. 11/382,849, Non-Final Office Action mailed May 12, 2010", 5 pgs.

"U.S. Appl. No. 11/382,849, Non-Final Office Action mailed Aug. 31, 2009", 8 pgs.

"U.S. Appl. No. 11/382,849, Notice of Allowance mailed Oct. 15, 2010", 6 pgs.

"U.S. Appl. No. 11/382,849, Response filed Apr. 26, 2010 to Final Office Action mailed Jan. 28, 2010", 10 pgs.

"U.S. Appl. No. 11/382,849, Response filed Jun. 8, 2009 to Restriction Requirement mailed May 6, 2009", 8 pgs.

"U.S. Appl. No. 11/382,849, Response filed Aug. 2, 2010 to Non Final Office Action mailed May 12, 2010", 7 pgs.
"U.S. Appl. No. 11/382,849, Response filed Nov. 30, 2009 to Non Final Office Action mailed Aug. 31, 2009", 11 pgs.
"U.S. Appl. No. 11/382,849, Restriction Requirement mailed May 6, 2009", 6 pgs.
"U.S. Appl. No. 11/458,286, Notice of Allowance mailed May 28, 2008", 7 pgs.
"U.S. Appl. No. 11/458,286, Notice of Allowance mailed Nov. 26, 2007", 7 pgs.
"U.S. Appl. No. 11/458,286, Preliminary Amendment mailed Feb. 26, 2008", 7 pgs.
"U.S. Appl. No. 11/682,448, Final Office Action mailed Oct. 7, 2010", 6 pgs.
"U.S. Appl. No. 11/682,448, Non-Final Office Action mailed Apr. 5, 2010", 16 pgs.
"U.S. Appl. No. 11/682,448, Response filed Jan. 7, 2011 to Final Office Action mailed Oct. 7, 2010", 14 pgs.
"U.S. Appl. No. 11/682,448, Response filed Feb. 7, 2011 to Final Office Action mailed Oct. 7, 2010 and Advisory Action mailed Feb. 4, 2011", 15 pgs.
"U.S. Appl. No. 11/682,448, Response filed Jul. 1, 2010 to Non Final Office Action mailed Apr. 5, 2010", 12 pgs.
"U.S. Appl. No. 11/682,448, Advisory Action mailed Feb. 4, 2011", 3 pgs.
"U.S. Appl. No. 11/868,767, Notice of Allowance mailed Mar. 24, 2010", 7 pgs.
"U.S. Appl. No. 11/868,767, Notice of Allowance mailed Sep. 17, 2010", 4 pgs.
"U.S. Appl. No. 12/250,868, Non Final Office Action mailed Feb. 8, 2011", 7 pgs.
"European Application Serial No. 06752527.9, Communication mailed Mar. 8, 2010", 6 pgs.
"European Application Serial No. 06717345.0, Communication dated Aug. 22, 2007", 2 pgs.
"European Application Serial No. 06717345.0, Office Action mailed May 15, 2009", 2 pgs.
"European Application Serial No. 06717345.0, Response filed Sep. 11, 2009 to Communication mailed May 15, 2009", 7 pgs.
"European Application Serial No. 06717345.0, Response filed Sep. 28, 2007 to Communication dated Aug. 22, 2007", 12 pgs.
"European Application Serial No. 06740227.1, Communication dated Dec. 27, 2007", 2 pgs.
"European Application Serial No. 06740227.1, Response filed Jan. 27, 2008 to Communication dated Dec. 27, 2007", 9 pgs.
"European Application Serial No. 06752527.9, Office Action Response mailed Jul. 7, 2010", 15 pgs.
"European Application Serial No. 06752527.9, Summons to Attend Oral Proceedings Received mailed Jul. 23, 2010", 3 pgs.
"European Application Serial No. 06752540.2, Communication Mar. 3, 2008", 2 pgs.
"European Application Serial No. 06752540.2, Communication mailed Mar. 8, 2010", 2 pgs.
"European Application Serial No. 06752540.2, Response filed Apr. 9, 2008 to Communication Mar. 3, 2008", 6 pgs.
"European Application Serial No. 06752540.2, Response filed Jul. 15, 2010 to Communication mailed Mar. 8, 2010", 20 pgs.
"European Application Serial No. 06762527.9, Communication pursuant to Rules 161 to 182 EPC mailed Mar. 3, 2008", 2 pgs.
"European Application Serial No. 06762527.9, Response filed Apr. 9, 2008 to Communication pursuant to Rules 161 to 182 EPC mailed Mar. 3, 2008", 6 pgs.
"European Application Serial No. 07797336.0, Communication mailed Mar. 10, 2010", 3 pgs.
"European Application Serial No. 07797336.0, Office Action mailed Feb. 24, 2009", 4 pgs.
"European Application Serial No. 07797336.0, Response filed Jul. 6, 2009 to Communication mailed Feb. 24, 2009", 20 pgs.
"European Application Serial No. 07797336.0, Response Filed Jul. 7, 2010 to Office Action dated Mar. 10, 2010", 5 pgs.
"European Application Serial No. 08726356.2, Office Action mailed May 31, 2010", 7 pgs.
"European Application Serial No. 08726356.2, Response filed Aug. 27, 2010 to Communication dated May 31, 2010", 14 pgs.
"European Application Serial No. 10166449.8-2305, European Search Report mailed Sep. 9, 2010", 5 pgs.
"International Application Serial No. PCT/US2006/000125, International Search Report and Written Opinion mailed May 11, 2006", 12 pgs.
"International Application Serial No. PCT/US2006/018497, International Search Report mailed Oct. 24, 2006", 5 pgs.
"International Application Serial No. PCT/US2006/018497, Written Opinion mailed Oct. 24, 2006", 7 pgs.
"International Application Serial No. PCT/US2006/018642, International Search Report and Written Opinion mailed Oct. 24, 2006", 14 pgs.
"International Application Serial No. PCT/US2007/068217, International Search Report mailed Oct. 30, 2007", 5 pgs.
"International Application Serial No. PCT/US2007/068217, Written Opinion mailed Oct. 30, 2007", 8 pgs.
"International Application Serial No. PCT/US2008/002799, Invitation to Pay Fees and Partial International Search Report mailed Jul. 14, 2008", 7 pgs.
"International Application Serial No. PCT/US2008/002799, Written Opinion mailed Oct. 15, 2008", 11 pgs.
"International Application Serial No. PCT/US2008/002799, International Search Report mailed Oct. 15, 2008", 6 pgs.
"International Application Serial No. PCT/US2006/011972, Search Report and Written Opinion mailed Oct. 6, 2006", 16 pgs.
"Japanese Application Serial No. 2008-511421, Voluntary Amendment filed Apr. 27, 2009", (w/ English Translation of Amended Claims), 11 pgs.
"Japanese Application Serial No. 2008-511452, Voluntary Amendment filed May 11, 2009", (w/ English Translation of Amended Claims), 8 pgs.
"Japanese Application Serial No. 2009-510093, Voluntary Amendment filed Jan. 14, 2009", 4 pgs.
"Japanese Application Serial No. 2009-552705, Amendment filed Oct. 21, 2009", (w/ English Translation), 43 pgs.
"Coronary Dilatation Catheters", [online]. [archived Mar. 3, 2006]. Retrieved from the Internet: <URL: http://web.archive.org/web/20060303151627/http://www.guidant.com/products/TemplatePDFs/NoPriceDilataticatheters.pdf>, (2006), 3 pgs.
Airaksinen, K. E., et al., "Antiarrhythmic effect of repeated coronary occlusion during balloon angioplasty", J Am Coll Cardiol., 29(5), (Apr. 1997), 1035-1038.
Amende, I., "Hemodynamics in ischemia: diastolic phase", Z. Kardiol., 73 Suppl 2, [Article in German With English Abstract], (1984), 127-33.
"Arrow Bipolar Pacing Catheters and Pacing Kits", Arrow International, (2000), 4 pgs.
Dzwonczyk, R., et al., "Myocardial electrical impedance responds to ischemia and reperfusion in humans", IEEE Transactions on Biomedical Engineering, 51(12), (Dec. 2004), 2206-2209.
Henriques, Jose P., et al., "Outcome of primary angioplasty for acute myocardial infarction during routine duty hours versus during off-hours", J Am Coll Cardiol, 41(12), (Jun. 18, 2003), 2138-2142.
Ishihara, M., et al., "Implications of prodromal angina pectoris in anterior wall acute myocardial infarction: acute angiographic findings and long-term prognosis", J Am Coll Cardiol., 30(4), (1997), 970-5.
Kin, Hajime, et al., "Postconditioning attenuates myocardial ischemia-reperfusion injury by inhibiting events in the early minutes of reperfusion", Cardiovascular Research, 62(1), (Apr. 1, 2004), 74-85.
Kis, A., "Repeated cardiac pacing extends the time during which canine hearts are protected against ischaemia-induced arrhythmias : role of nitric oxide.", Journal of Molecular and Cellular Cardiology, 31(6), (Jun. 1999), 1229-1241.
Kloner, R. A., et al., "Prospective temporal analysis of the onset of preinfarction angina versus outcome: an ancillary study in TIMI-9B", Circulation, 97(11), (1998), 1042-5.
Koning, M M, "Rapid ventricular pacing produces myocardial protection by nonischemic activation of KATP+ channels", Circulation, 93(1), (Jan. 1, 1996), 178-186.

Krayenbuhl, H. P., "Hemodynamics in ischemia. Systolic phase", Z. Kardiol., 73 Suppl 2, [Article in German with English Abstract], (1984), 119-25.

Loukogeorgakis, S. P., et al., "Remote ischemic preconditioning provides early and late protection against endothelial ischemia-reperfusion injury in humans: role of the autonomic nervous system.", J Am Coll Cardiol., 46(3), (Aug. 2, 2005), 450-6.

Makhoul, John, "Linear Prediction: A Tutorial Review", Proceedings of the IEEE, 63, (Apr. 1975), 561-580.

Meier, B., et al., "Coronary Pacing During Percutaneous Transluminal Coronary Angioplasty", Circulation, 71(3), (Mar. 1985), 557-561.

Murry, C. E., et al., "Preconditioning with ischemia: a delay of lethal cell injury in ischemic myocardium", Circulation, 74(5), (1986), 1124-1136.

Ovize, M., et al., "Stretch preconditions canine myocardium.", Am J Physiol., 266(1 Pt 2), (Jan. 1994), H137-46.

Panju, Akbar A, et al., "Is This Patient Having a Myocardial Infarction?", JAMA, 280(14), (Oct. 14, 1998), 1256-1263.

Prinzen, Frits W, "Mapping of regional myocardial strain and work during ventricular pacing: experimental study using magnetic resonance imaging tagging", Journal of the American College of Cardiology, 33(6), (May 1999), 1735-1742.

Rosa, A., et al., "Ectopic Pacing at Physiological Rate Improves Postanoxic Recovery of the Developing Heart", Am. J. Physiol.—Heart Circ. Physiol., 284, (2003), H2384-H2392.

Salerno, D. M., "Seismocardiography for monitoring changes in left ventricular function during ischemia.", Chest, 100(4), (Oct. 1991), 991-3.

Solomon, S. D., et al., "Angina pectoris prior to myocardial infarction protects against subsequent left ventricular remodeling", J Am Coll Cardiol., 43(9), (2004), 1511-4.

Tavel, Morton E, "The Appearance of Gallop Rhythm after Exercise Stress Testing", Clin. Cardiol., vol. 19, (1996), 887-891.

Tsang, A., et al., "Postconditioning: a form of "modified reperfusion" protects the myocardium by activating the phosphatidylinositol 3-kinase-Akt pathway", Circ Res., 95(3), Epub Jul. 8, 2004, (Aug. 6, 2004), 230-2.

Vanagt, W. Y. R., et al., "Ventricular Pacing for Improving Myocardial Tolerance to Ischemia", Progress Report on Project Guidant—CARIM, (Oct. 2003), 1-25.

Vegh, A, et al., "Transient ischaemia induced by rapid cardiac pacing results in myocardial preconditioning", Cardiovascular Research, 25(12), (Dec. 1991), 1051-3.

Wu, Zhong-Kai, et al., "Ischemic preconditioning suppresses ventricular tachyarrhythmias after myocardial revascularization", Circulation, 106(24), (Dec. 10, 2002), 3091-3096.

Yang, S. M., et al., "Multiple, brief coronary occlusions during early reperfusion protect rabbit hearts by targeting cell signaling pathways", Journal of the American College of Cardiology, 44(5), (Sep. 1, 2004), 1103-1110.

Zhi-Qing, Z., et al., "Inhibition of myocardial injury by ischemic postconditioning during reperfusion: comparison with ischemic preconditioning", Am J Physiol Heart Circ Physiol, 285(2), (Aug. 2003), H579-H588.

U.S. Appl. No. 13/113,706, filed May 23, 2011, Method and Apparatus for Pacing During Revascularization.

U.S. Appl. No. 13/231,152, filed Sep. 13, 2011, Ischemia Detection Using a Heart Sound Sensor.

"U.S. Appl. No. 12/322,382, Advisory Action mailed Nov. 8, 2011", 3 pgs.

"U.S. Appl. No. 12/322,382, Final Office Action mailed Aug. 25, 2011", 12 pgs.

"U.S. Appl. No. 12/322,382, Non Final Office Action mailed Mar. 21, 2011", 14 pgs.

"U.S. Appl. No. 12/322,382, Response filed Jun. 21, 2011 to Non Final Office Action mailed Mar. 21, 2011", 16 pgs.

"U.S. Appl. No. 12/322,382, Response filed Oct. 24, 2011 to Final Office Action mailed Aug. 25, 2011", 15 pgs.

"U.S. Appl. No. 12/830,534 , Response filed Apr. 9, 2012 to Final Office Action mailed Feb. 7, 2012", 11 pgs.

"U.S. Appl. No. 12/830,534, Advisory Action mailed Apr. 24, 2012", 3 pgs.

"U.S. Appl. No. 12/830,534, Final Office Action mailed Feb. 7, 2012", 12 pgs.

"U.S. Appl. No. 12/830,534, Non Final Office Action mailed Aug. 22, 2011", 13 pgs.

"U.S. Appl. No. 12/830,534, Response filed Nov. 22, 2011 to Non Final Office Action mailed Aug. 22, 2011", 13 pgs.

"U.S. Appl. No. 13/019,888, Non Final Office Action mailed Jun. 29, 2012", 9 pgs.

"U.S. Appl. No. 13/019,888, Response to Restriction Requirement mailed Apr. 2, 2012", 8 pgs.

"U.S. Appl. No. 13/019,888, Restriction Requirement mailed Apr. 2, 2012", 5 pgs.

"U.S. Appl. No. 13/113,706, Non Final Office Action Mailed Dec. 21, 2011", 6 pgs.

"U.S. Appl. No. 13/113,706, Response filed Mar. 21, 2012 to Non Final Office Action mailed Dec. 21, 2011", 14 pgs.

"European Application Serial No. 06740227.1, Office Action mailed Mar. 10, 2011", 4 pgs.

"European Application Serial No. 06740227.1, Response filed Jul. 12, 2011 to Office Action dated Mar. 10, 2011", 15 pgs.

"European Divisional Application Serial No. 10166449.8, Response filed Mar. 14, 2011 to EP Search Report mailed Sep. 9, 2010", 10 pgs.

"Japanese Application Serial No. 2007-550428, Office Action mailed Apr. 9, 2012", Partial English Translation, 5 pgs.

"Japanese Application Serial No. 2007-550428, Office Action mailed Aug. 3, 2011", (w/ English Translation), 4 pgs.

"Japanese Application Serial No. 2007-550428. Response filed Nov. 1, 2011 to Office Action mailed Aug. 3, 2011", (w/ English Translation of Amended Claims), 6 pgs.

"Japanese Application Serial No. 2008-508872, Office Action mailed Oct. 27, 2011", 6 pgs.

"Japanese Application Serial No. 2008-508872, Response filed Jan. 31, 2012 to Office Action mailed Oct. 31, 2011", W/English Translation, 14 pgs.

"Japanese Application Serial No. 2008-511421, Office Action mailed Nov. 16, 2011", (w/ English Translation), 5 pgs.

"Japanese Application Serial No. 2008-511421, Response filed Mar. 14, 2012 to Office Action mailed Nov. 16, 2011", (w/ English Translation of Amended Claims), 16 pgs.

"Japanese Application Serial No. 2008-511452, Office Action mailed Nov. 14, 2011", 4 pgs.

"Japanese Application Serial No. 2008-511452, Response filed Feb. 14, 2012 to Office Action mailed Nov. 14, 2011", (English Translation of Claims), 3 pgs.

"Japanese Application Serial No. 2009-510093, Office Action mailed Mar. 12, 2012", (w/ English Translation), 9 pgs.

"Japanese Application Serial No. 2009-510093, Response filed Jun. 11, 2012 to Office Action mailed Mar. 12, 2012", English Claims with response, 11 pgs.

Kis, A., et al., "Repeated Cardiac Pacing Extends the Time During Which Canine Hearts are Protected Against Ischaemia-induced Arrhythmias: Role of Nitric Oxide", Journal of Molecular and Cellular, 31(6), (1999), 1229-1241.

* cited by examiner

METHOD AND APPARATUS FOR CARDIAC PROTECTION PACING

CLAIM OF PRIORITY

This application is a division of and claims the benefit of priority under 35 U.S.C. §120 to U.S. patent application Ser. No. 11/129,050, filed on May 13, 2005, now issued as U.S. Pat. No. 7,917,210, which is hereby incorporated by reference herein in its entirety.

CROSS-REFERENCE TO RELATED APPLICATIONS

This application is related to commonly assigned, U.S. patent application Ser. No. 11/030,575, entitled "INTERMITTENT AUGMENTATION PACING FOR CARDIOPROTECTIVE EFFECT," filed on Jan. 6, 2005, now issued as U.S. Pat. No. 7,295,874, U.S. patent application Ser. No. 11/113,828, entitled "METHOD AND APPARATUS FOR PACING DURING REVASCULARIZATION," filed on Apr. 25, 2005, now issued as U.S. Pat. No. 7,962,208, and U.S. patent application Ser. No. 11/129,058, entitled "METHOD AND APPARATUS FOR DELIVERING PACING PULSES USING A CORONARY STENT," filed on May 13, 2005, which are hereby incorporated by reference in their entirety.

TECHNICAL FIELD

This document relates generally to cardiac pacing systems and particularly to a system for delivering pacing pulses to protect the heart from injuries associated with ischemic events.

BACKGROUND

The heart is the center of a person's circulatory system. It includes an electro-mechanical system performing two major pumping functions. The left portions of the heart draw oxygenated blood from the lungs and pump it to the organs of the body to provide the organs with their metabolic needs for oxygen. The right portions of the heart draw deoxygenated blood from the body organs and pump it to the lungs where the blood gets oxygenated. These pumping functions are resulted from contractions of the myocardium. In a normal heart, the sinoatrial node, the heart's natural pacemaker, generates electrical impulses that propagate through an electrical conduction system to various regions of the heart to excite the myocardial tissues of these regions. Coordinated delays in the propagations of the electrical impulses in a normal electrical conduction system cause the various portions of the heart to contract in synchrony to result in efficient pumping functions. A blocked or otherwise abnormal electrical conduction and/or deteriorated myocardial tissue cause dysynchronous contraction of the heart, resulting in poor hemodynamic performance, including a diminished blood supply to the heart and the rest of the body. The condition where the heart fails to pump enough blood to meet the body's metabolic needs is known as heart failure.

Myocardial infarction (MI) is the necrosis of portions of the myocardial tissue resulted from cardiac ischemia, a condition in which the myocardium is deprived of adequate oxygen and metabolite removal due to an interruption in blood supply caused by an occlusion of a blood vessel such as a coronary artery. The necrotic tissue, known as infarcted tissue, loses the contractile properties of the normal, healthy myocardial tissue. Consequently, the overall contractility of the myocardium is weakened, resulting in an impaired hemodynamic performance. Following an MI, cardiac remodeling starts with expansion of the region of infarcted tissue and progresses to a chronic, global expansion in the size and change in the shape of the entire left ventricle. The consequences include a further impaired hemodynamic performance and a significantly increased risk of developing heart failure, as well as a risk of suffering recurrent MI.

Therefore, there is a need to protect the myocardium from injuries associated with ischemic events, including MI.

SUMMARY

A pacing system delivers cardiac protection pacing to protect the heart from injuries associated with ischemic events. The pacing system detects an ischemic event and, in response, initiates one or more cardiac protection pacing sequences each including alternative pacing and non-pacing periods.

In one embodiment, a cardiac pacing system includes a sensing circuit, an ischemia detector, a pulse output circuit, and a control circuit. The sensing circuit senses one or more signals indicative of an ischemic event. The ischemia detector detects the ischemic event from the one or more signals. The pulse output circuit delivers pacing pulses. The control circuit controls the delivery of the pacing pulses and includes a cardiac protection pacing sequence initiator and a cardiac protection pacing timer. The cardiac protection pacing sequence initiator initiates one or more cardiac protection pacing sequences in response to the detection of the ischemic event. The one or more cardiac protection pacing sequences each include alternating pacing and non-pacing periods. The pacing periods each have a pacing duration during which a plurality of the pacing pulses is delivered. The non-pacing periods each have a non-pacing duration during which none of the pacing pulses is delivered. The cardiac protection pacing timer times the one or more cardiac protection pacing sequences.

In one embodiment, a method for delivering the cardiac protection pacing is provided. One or more signals indicative of an ischemic event are sensed. The ischemic event is detected from the one or more signals. One or more cardiac protection pacing sequences are initiated in response to the detection of the ischemic event. The one or more cardiac protection pacing sequences each include alternating pacing and non-pacing periods. The pacing periods each have a pacing duration during which a plurality of pacing pulses is delivered. The non-pacing periods each have a non-pacing duration during which no pacing pulse is delivered. The plurality of pacing pulses is delivered during each of the pacing periods.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses a pacing system including an implantable medical device that delivers pacing pulses to protect the heart from injuries associated with ischemic events, including MI. The pacing pulses are delivered to the heart to change the distribution of stress in the myocardium, thereby triggering the intrinsic myocardial protective mechanism against ischemic damage to the myocardial tissue. In one embodiment, the implantable medical device detects ischemic events. In response to the detection of an ischemic event, a cardiac protection pacing sequence is initiated to protect the heart from ischemic damage caused by the detected ischemic event by delivering a pacing postconditioning therapy. Then, additional cardiac protection pacing sequences are initiated to protect the heart from ischemic damage caused by potentially recurrent ischemic events by delivering a prophylactic pacing preconditioning therapy. The pacing postconditioning therapy and the prophylactic pacing preconditioning therapy each include delivery of one or more cardiac protection pacing sequences each including alternating pacing and non-pacing periods. The pacing periods each have a pacing duration during which a plurality of pacing pulses is delivered. The non-pacing periods each have a non-pacing duration during which no pacing pulses is delivered. In other words, the pacing postconditioning therapy and the prophylactic pacing preconditioning therapy each include intermittent delivery of pacing pulses over a predetermined duration.

Figure 1:
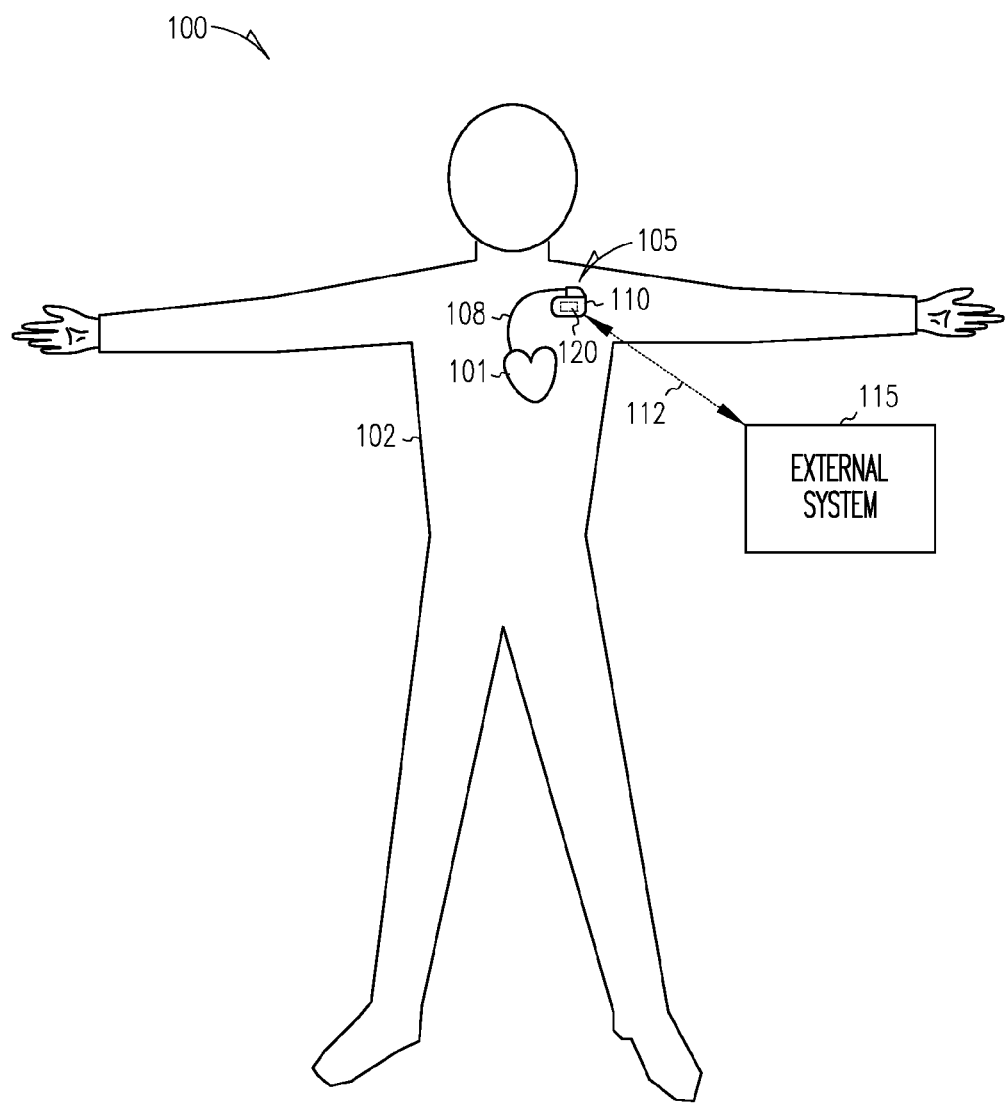
FIG. 1 is an illustration of an embodiment of a cardiac rhythm management (CRM) system including an implantable system and an external system and portions of an environment in which the CRM system is used.

FIG. 1 is an illustration of an embodiment of a cardiac rhythm management (CRM) system 100 and portions of an environment in which system 100 is used. System 100 includes an implantable system 105, an external system 115, and a telemetry link 112 providing for communication between implantable system 105 and external system 115.

Implantable system 105 includes, among other things, implantable medical device 110 and lead system 108. In various embodiments, implantable medical device 110 is an implantable CRM device including one or more of a pacemaker, a cardioverter/defibrillator, a cardiac resynchronization therapy (CRT) device, a cardiac remodeling control therapy (RCT) device, a neurostimulator, a drug delivery device or a drug delivery controller, and a biological therapy device. As illustrated in FIG. 1, implantable medical device 110 is implanted in a body 102. In various embodiments, lead system 108 includes leads for sensing physiological signals and delivering pacing pulses, cardioversion/defibrillation shocks, neurostimulation pulses, pharmaceutical agents, biological agents, and/or other types of energy or substance for treating cardiac disorders. In one embodiment, lead system 108 includes one or more pacing-sensing leads each including at least one electrode placed in or on a heart 101 for sensing electrogram and/or delivering pacing pulses. In other embodiments, electrodes placed in body 102 but away from heart 101 are used to sense physiological signals and deliver pacing pulses, cardioversion/defibrillation shocks, neurostimulation pulses, pharmaceutical agents, biological agents, and/or other types of energy or substance for treating cardiac disorders. In a specific embodiment, one or more electrodes are incorporated onto implantable medical device 110 for subcutaneous placement.

Implantable medical device 110 includes a cardiac pacing system 120. Cardiac pacing system 120 is capable of delivering cardiac protection pacing therapies through lead system 108. The delivery of a cardiac protection pacing therapy is timed as a cardiac protection pacing sequence including alternating pacing and non-pacing periods. In one embodiment, in addition to the cardiac protection pacing therapy, cardiac pacing system 120 also delivers one or more other cardiac pacing therapies, such a bradycardia pacing therapy, CRT, and RCT. If another pacing therapy is being delivered when a cardiac protection pacing sequence is to be initiated, that pacing therapy is temporarily suspended to allow the delivery of the cardiac protection pacing therapy and resumed upon completion of the cardiac protection pacing sequence.

External system 115 allows a user such as a physician or other caregiver or a patient to control the operation of implantable medical device 110 and obtain information acquired by implantable medical device 110. In one embodiment, external system 115 includes a programmer communicating with implantable medical device 110 bi-directionally via telemetry link 112. In another embodiment, external system 115 is a patient management system including an external device communicating with a remote device through a telecommunication network. The external device is within the vicinity of implantable medical device 110 and communicates with implantable medical device 110 bi-directionally via telemetry link 112. The remote device allows the user to monitor and treat a patient from a distant location. The patient monitoring system is further discussed below, with reference to FIG. 5.

Telemetry link 112 provides for data transmission from implantable medical device 110 to external system 115. This includes, for example, transmitting real-time physiological data acquired by implantable medical device 110, extracting physiological data acquired by and stored in implantable medical device 110, extracting therapy history data stored in implantable medical device 110, and extracting data indicating an operational status of implantable medical device 110

(e.g., battery status and lead impedance). Telemetry link 112 also provides for data transmission from external system 115 to implantable medical device 110. This includes, for example, programming implantable medical device 110 to acquire physiological data, programming implantable medical device 110 to perform at least one self-diagnostic test (such as for a device operational status), and programming implantable medical device 110 to deliver at least one therapy.

Figure 2:
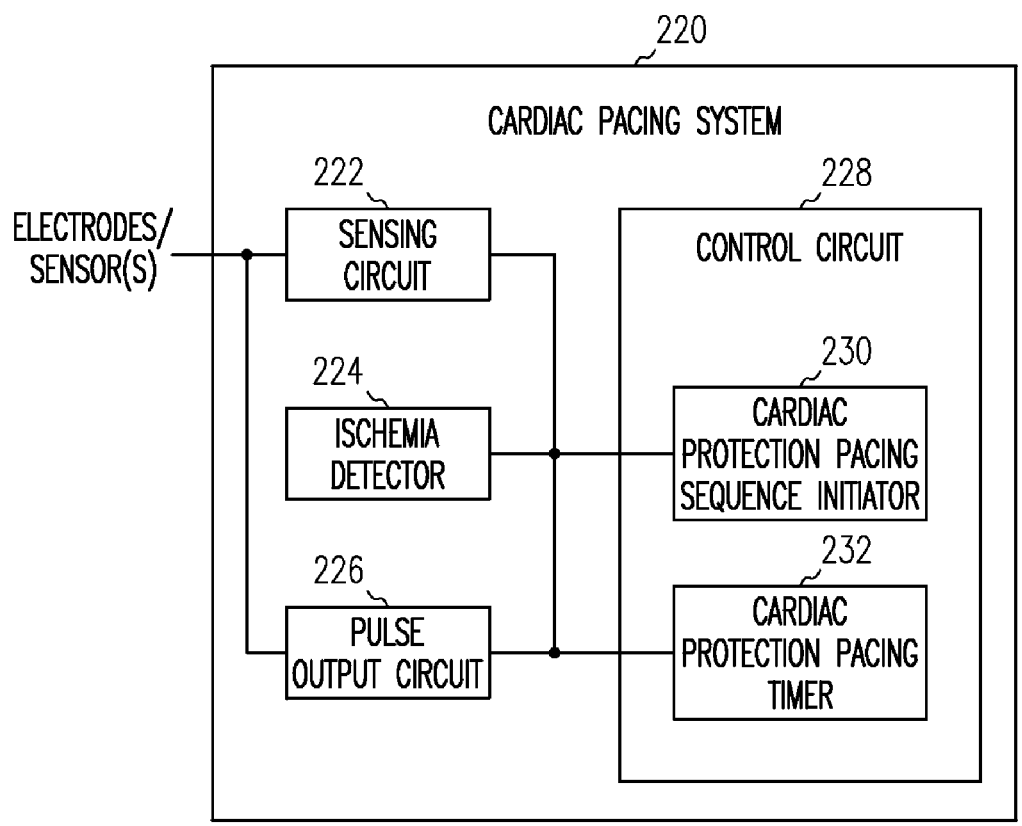
FIG. 2 is a block diagram illustrating an embodiment of portions of the circuit of a cardiac pacing system of the implantable system.

FIG. 2 is a block diagram illustrating an embodiment of portions of the circuit of a cardiac pacing system 220. Cardiac pacing system 220 is a specific embodiment of cardiac pacing system 120 and includes a sensing circuit 222, an ischemia detector 224, a pulse output circuit 226, and a control circuit 228. Sensing circuit 222 senses one or more signals using a plurality of electrodes and/or one or more sensors. The one or more signals are indicative of ischemic events. Ischemia detector 224 detects the ischemic events from the one or more signals. Pulse output circuit 226 delivers pacing pulses to heart 101. Control circuit 228 controls the delivery of the pacing pulses based on the one or more sensed signals and/or in response to the detection of each ischemic event. In various embodiments, cardiac pacing system 220 is substantially contained in an implantable housing of implantable medical device 110.

Control circuit 228 includes a cardiac protection pacing sequence initiator 230 and a cardiac protection pacing timer 232. Cardiac protection pacing sequence initiator 230 initiates one or more cardiac protection pacing sequences in response to the detection of each ischemic event. The one or more cardiac protection pacing sequences each include alternating pacing and non-pacing periods. The pacing periods each have a pacing duration during which a plurality of pacing pulse is delivered. The non-pacing periods each have a non-pacing duration during which no pacing pulse is delivered. Once a cardiac protection pacing sequence is initiated, cardiac protection pacing timer 232 times that sequence. The one or more cardiac protection pacing sequences each have a sequence duration in a range of approximately 30 seconds to 1 hour. The pacing duration is in a range of approximately 5 seconds to 10 minutes. The non-pacing duration is in a range of approximately 5 seconds to 10 minutes.

Figure 3:
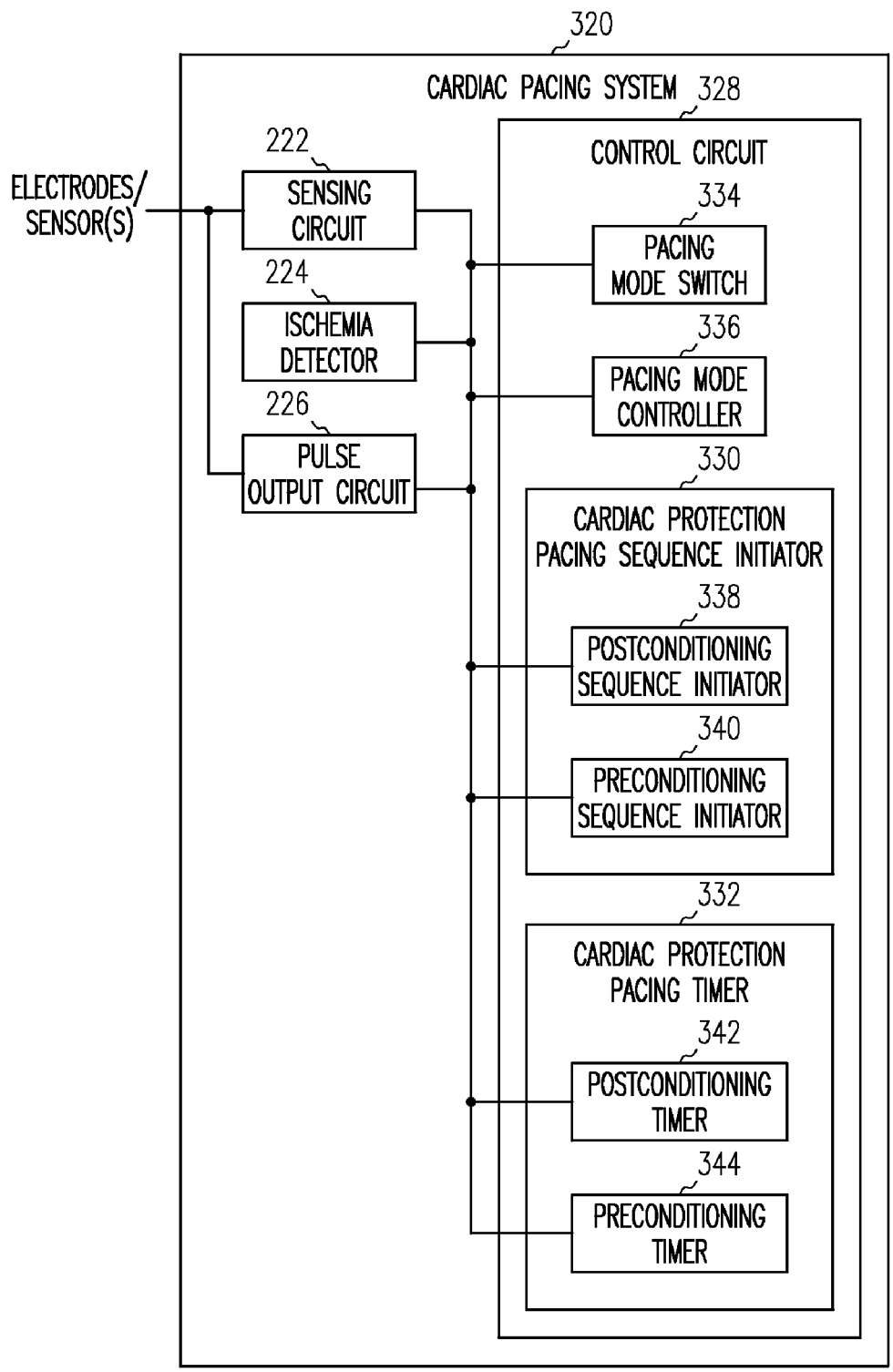
FIG. 3 is a block diagram illustrating a specific embodiment of portions of the circuit of the cardiac pacing system.

FIG. 3 is a block diagram illustrating an embodiment of portions of the circuit of a cardiac pacing system 320. Cardiac pacing system 320 is a specific embodiment of cardiac pacing system 220 and includes sensing circuit 222, ischemia detector 224, pulse output circuit 226, and a control circuit 328. Sensing circuit 222 senses the one or more signals indicative of the ischemic events. Ischemia detector 224 detects the ischemic events from the one or more signals. Pulse output circuit 226 delivers the pacing pulses to heart 101. Control circuit 328 controls the delivery of the pacing pulses based on the one or more sensed signals and/or in response to the detection of each ischemic event. In various embodiments, cardiac pacing system 320 is substantially contained in an implantable housing of implantable medical device 110.

Ischemia detector 224 includes an ischemia analyzer running an automatic ischemia detection algorithm to detect the ischemic event from the one or more signals. In one embodiment, ischemia detector 224 produces an ischemia alert signal indicative of the detection of each ischemic event. The ischemia signal is transmitted to external system 115 for producing an alarm signal and/or a warning message for the patient and/or a physician or other caregiver.

In one embodiment, ischemia detector 224 detects the ischemic events from one or more cardiac signals. Sensing circuit 222 includes a cardiac sensing circuit. In a specific example, cardiac signals are sensed using a wearable vest including embedded electrodes configured to sense surface biopotential signals indicative of cardiac activities. The sensed surface biopotential signals are transmitted to implantable medical device 110 via telemetry. In another specific embodiment, ischemia detector 224 detects the ischemic events from one or more wireless electrocardiogram (ECG) signals. Sensing circuit 222 includes a wireless ECG sensing circuit. A wireless ECG is a signal approximating the surface ECG and is acquired without using surface (skin contact) electrodes. An example of a circuit for sensing the wireless ECG is discussed in U.S. patent application Ser. No. 10/795,126, entitled "WIRELESS ECG IN IMPLANTABLE DEVICES," filed on Mar. 5, 2004, now issued as U.S. Pat. No. 7,299,085, assigned to Cardiac Pacemakers, Inc., which is incorporated by reference in its entirety. An example of a wireless ECG-based ischemia detector is discussed in U.S. patent application Ser. No. 11/079,744, entitled "CARDIAC ACTIVATION SEQUENCE MONITORING FOR ISCHEMIA DETECTION," filed on Mar. 14, 2005, now issued as U.S. Pat. No. 7,797,036, assigned to Cardiac Pacemakers, Inc., which is incorporated by reference in its entirety. In another embodiment, ischemia detector 224 detects the ischemic events from one or more electrogram signals. Sensing circuit 222 includes an electrogram sensing circuit. Examples of an electrogram-based ischemia detector are discussed in U.S. Pat. No. 6,108, 577, entitled, "METHOD AND APPARATUS FOR DETECTING CHANGES IN ELECTROCARDIOGRAM SIGNALS," and U.S. patent application Ser. No. 09/962,852, entitled "EVOKED RESPONSE SENSING FOR ISCHEMIA DETECTION," filed on Sep. 25, 2001, now issued as U.S. Pat. No. 7,340,303, both assigned to Cardiac Pacemakers, Inc., which are incorporated herein by reference in their entirety.

In another embodiment, ischemia detector 224 detects the ischemic events from one or more impedance signals. Sensing circuit 222 includes an impedance sensing circuit to sense one or more impedance signals each indicative of a cardiac impedance or a transthoracic impedance. Ischemia detector 224 includes an electrical impedance based sensor using a low carrier frequency to detect the ischemic events from an electrical impedance signal. Tissue electrical impedance has been shown to increase significantly during ischemia and decrease significantly after ischemia, as discussed in Dzwonczyk, et al. *IEEE Trans. Biomed. Eng.*, 51(12): 2206-09 (2004). The ischemia detector senses low frequency electrical impedance signal between electrodes interposed in the heart, and detects the ischemia as abrupt changes in impedance (such as abrupt increases in value).

In another embodiment, ischemia detector 224 detects the ischemic events from one or more signals indicative of heart sounds. Sensing circuit 222 includes a heart sound sensing circuit. The heart sound sensing circuit senses the one or more signals indicative of heart sounds using one or more sensors such as accelerometers and/or microphones. Such sensors are included in implantable medical device 110 or incorporated into lead system 108. Ischemia detector 224 detects the ischemic event by detecting predetermined type heart sounds, predetermined type heart sound components, predetermined type morphological characteristics of heart sounds, or other characteristics of heart sounds indicative of ischemia.

In another embodiment, ischemia detector 224 detects the ischemic events from one or more pressure signals. Sensing circuit 222 includes a pressure sensing circuit coupled to one or more pressure sensors. In a specific embodiment, the pressure sensor is an implantable pressure sensor sensing a signal indicative of an intracardiac or intravascular pressure whose characteristics are indicative of ischemia.

In another embodiment, ischemia detector 224 detects the ischemic event from one or more acceleration signals each indicative of regional cardiac wall motion. Sensing circuit 222 includes a cardiac motion sensing circuit coupled to one or more accelerometers each incorporated into a portion of a lead positioned on or in the heart. The ischemia detector detects ischemia as an abrupt decrease in the amplitude of local cardiac accelerations.

In another embodiment, ischemia detector 224 detects the ischemic event from a heart rate variability (HRV) signal indicative of HRV. Sensing circuit 222 includes an HRV sensing circuit 760 to sense the HRV and produce the HRV signal, which is representative of an HRV parameter. HRV is the beat-to-beat variance in cardiac cycle length over a period of time. The HRV parameter includes any parameter being a measure of the HRV, including any qualitative expression of the beat-to-beat variance in cardiac cycle length over a period of time. In a specific embodiment, the HRV parameter includes the ratio of Low-Frequency (LF) HRV to High-Frequency (HF) HRV (LF/HF ratio). The LF HRV includes components of the HRV having frequencies between about 0.04 Hz and 0.15 Hz. The HF HRV includes components of the HRV having frequencies between about 0.15 Hz and 0.40 Hz. The ischemia detector detects ischemia when the LF/HF ratio exceeds a predetermined threshold. An example of an LF/HF ratio-based ischemia detector is discussed in U.S. patent application Ser. No. 10/669,168, entitled "METHOD FOR ISCHEMIA DETECTION BY IMPLANTABLE CARDIAC DEVICE," filed on Sep. 23, 2003, now issued as U.S. Pat. No. 7,215,992, assigned to Cardiac Pacemakers, Inc., which is incorporated by reference in its entirety.

Control circuit 328 is a specific embodiment of control circuit 228 and includes a pacing mode switch 334, a pacing mode controller 336, a cardiac protection pacing sequence initiator 330, and a cardiac protection pacing timer 332. Control circuit 328 allows cardiac pacing system 320 to control the delivery of the cardiac protection pacing therapy as well as other pacing therapies. This allows the function of cardiac protection pacing to be included in an implantable medical device that delivers pacing therapies on a long-term basis, such as for treatment of bradycardia and heart failure. In various embodiments, cardiac protection pacing therapy includes a temporary pacing therapy delivered for one or more brief periods in response to the detection of each ischemia event, and the implantable medical device also delivers a chronic pacing therapy such as a bradycardia pacing therapy, CRT, or RCT. In other embodiments, the cardiac protection pacing therapy is the only pacing therapy delivered, or the cardiac protection pacing therapy is the only pacing therapy programmed to be delivered for at least a certain period of time.

Each pacing therapy is delivered by delivering pacing pulses in accordance with a predetermined pacing mode. Pacing mode switch 334 switches the pacing mode from a chronic pacing mode to a temporary pacing mode when a cardiac protection pacing sequence is initiated and to switch the pacing mode from the temporary pacing mode to the chronic pacing mode when the cardiac protection pacing sequence is completed. Pacing mode controller 336 controls the delivery of the pacing pulses from pulse output circuit 226 according to the pacing mode as selected by pacing mode switch 334. The temporary pacing mode refers to the pacing mode used in a cardiac protection pacing therapy, which is a temporary pacing therapy. The chronic pacing mode refers to the pacing mode used in a chronic pacing therapy such as a bradycardia pacing therapy, CRT, or RCT. In one embodiment, the temporary pacing mode is substantially different from the chronic pacing mode, such that the cardiac protection pacing therapy changes the distribution of stress in the myocardium, thereby triggering the intrinsic myocardial protective mechanism against ischemic damage to the myocardial tissue. Examples of the temporary pacing mode include VOO, VVI, VDD, and DDD modes, including their rate-responsive versions if applicable. In one embodiment, the pacing rate is set to be about 20 pulses per minute higher than the patient's intrinsic heart rate during the temporary pacing mode. In a specific embodiment, if the cardiac protection pacing therapy is the only pacing therapy being delivered (in other words, the chronic pacing mode is a non-pacing mode), the temporary pacing mode is an atrial tracking pacing mode such as the VDD or DDD mode, including their rate-responsive and multi-ventricular site versions. If the chronic pacing mode is an atrial tracking pacing mode such as the VDD or DDD mode, the temporary pacing mode is a VOO or VVI mode at with a pacing rate higher than the patient's intrinsic heart rate or a VDD or DDD mode with substantially different pacing parameter such as a pacing rate, pacing sites, and/or atrioventricular pacing delays.

Cardiac protection pacing sequence initiator 330 is a specific embodiment of cardiac protection pacing sequence initiator 230 and initiates one or more cardiac protection pacing sequences in response to the detection of each ischemic event. In one embodiment, cardiac protection pacing sequence initiator 330 also initiates one or more cardiac protection pacing sequences in response to one or more commands issued by the user through external system 115. For example, following a diagnosis of vulnerable plaque indicative of a high risk for MI, a physician applies a pacing preconditioning therapy by starting a cardiac protection pacing sequence by issuing such a command. Cardiac protection pacing timer 332 times the one or more cardiac protection pacing sequences including the alternating pacing and non-pacing periods.

In one embodiment, the one or more cardiac protection pacing sequences initiated in response to the detection of each ischemic event include at least one postconditioning sequence and a plurality of prophylactic preconditioning sequences. As illustrated in FIG. 3, cardiac protection pacing sequence initiator 330 includes a postconditioning sequence initiator 338 and a preconditioning sequence initiator 340, and cardiac protection pacing timer 332 includes a postconditioning timer 342 and a preconditioning timer 344.

Postconditioning sequence initiator 338 initiates the postconditioning sequence in response to the detection of an ischemic event. In one embodiment, postconditioning sequence initiator 338 initiates the postconditioning sequence when the end of the ischemic event is detected. In one embodiment, the end of the ischemic event is detected when the ischemic event is no longer detected by ischemia detector 224. In one embodiment, postconditioning sequence initiator 338 initiates the postconditioning pacing sequence when a post-ischemia time interval expires. The post-ischemia time interval starts when the end of the ischemic event is detected and is up to approximately 10 minutes, with approximately 30 seconds being a specific example. In one embodiment, the post-ischemia time interval is chosen such that the postconditioning pacing sequence is initiated after the reperfusion phase following the ischemic event has started. In another embodiment, postconditioning sequence initiator 338 initiates the postconditioning pacing sequence in response to one or more postconditioning commands issued by the user.

Preconditioning sequence initiator 340 initiates the prophylactic preconditioning sequences, one at a time, after the end of the ischemic event is detected and the postconditioning sequence is completed. In one embodiment, preconditioning sequence initiator 340 initiates the prophylactic preconditioning pacing sequences on a periodic basis using a predetermined period. The predetermined period is in a range of approximately 24 hours to 72 hours, with approximately 48 hours being a specific example. In another embodiment, preconditioning sequence initiator 340 initiates the prophylactic preconditioning pacing sequences according to a programmed preconditioning schedule. In another embodiment, preconditioning sequence initiator 340 initiates the prophylactic preconditioning pacing sequences in response to one or more preconditioning commands issued by the user.

Postconditioning timer 342 times the postconditioning sequence including alternating postconditioning pacing and non-pacing periods. The postconditioning pacing periods each have a postconditioning pacing duration during which a plurality of pacing pulses is delivered. The postconditioning non-pacing periods each have a postconditioning non-pacing duration during which no pacing pulse is delivered. The postconditioning sequence has a postconditioning sequence duration in a range of approximately 30 seconds to 1 hour, with approximately 10 minutes being a specific example. The postconditioning pacing duration is in a range of approximately 5 seconds to 10 minutes, with approximately 30 seconds being a specific example. The postconditioning non-pacing duration is in a range of approximately 5 seconds to 10 minutes, with approximately 30 seconds being a specific example.

Preconditioning timer 344 times the prophylactic preconditioning pacing sequences including alternating preconditioning pacing and non-pacing periods. The preconditioning pacing periods each have a preconditioning pacing duration during which a plurality of pacing pulse is delivered. The preconditioning non-pacing periods each have a preconditioning non-pacing duration during which no pacing pulse is delivered. The prophylactic preconditioning pacing sequences each have a preconditioning sequence duration in a range of approximately 10 minutes to 1 hour, with approximately 40 minutes being a specific example. The preconditioning pacing duration is in a range of approximately 1 minute to 30 minutes, with approximately 5 minutes being a specific example. The preconditioning non-pacing duration is in a range of approximately 1 minute to 30 minutes, with approximately 5 minutes being a specific example.

In one embodiment, control circuit 328 detects an arrhythmia and suspends the one or more cardiac protection pacing sequences in response to the detection of the arrhythmia. Control circuit 328 includes an arrhythmia detector to detect one or more predetermined types of arrhythmia. In one embodiment, cardiac protection pacing sequence initiator 330 cancels, holds, or otherwise adjusts the timing of the initiation of a cardiac protection pacing sequence in response to a detection of arrhythmia. In one embodiment, cardiac protection pacing timer 332 terminates or suspends a cardiac protection pacing sequence in response to the detection of an arrhythmia that occurs during the cardiac protection pacing sequence. In a specific embodiment, postconditioning sequence initiator 338 cancels the initiation of a postconditioning sequence in response to the detection of arrhythmia. In a specific embodiment, preconditioning sequence initiator 340 holds the initiation of a prophylactic preconditioning pacing sequence in response to the detection of arrhythmia unit the arrhythmia is no longer detected.

In one embodiment, cardiac protection pacing timer 332 terminates or suspends a cardiac protection pacing sequence in response to the detection of an arrhythmia that occurs during the cardiac protection pacing sequence.

Figure 4:
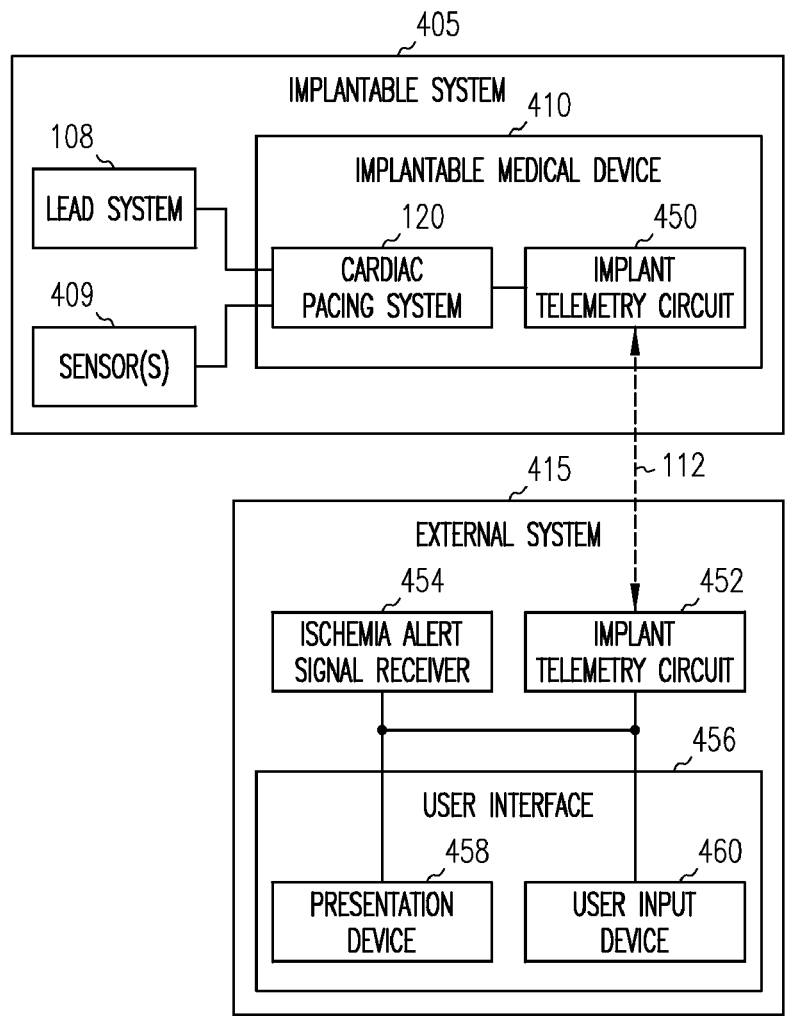
FIG. 4 is a block diagram illustrating an embodiment of portions of circuits of the implantable system and the external system.

FIG. 4 is a block diagram illustrating an embodiment of portions of circuits of an implantable system 405 and an external system 415. Implantable system 405 is a specific embodiment of implantable system 105. External system 415 is a specific embodiment of external system 115.

Implantable system 405 includes lead system 108, one or more sensors 409, and implantable medical device 410. Sensor(s) 409 includes electrodes, accelerometer(s), pressure sensor(s), and/or other sensors for sensing one or more signals required for the operation of implantable medical device 410, including detection of ischemic events. In various embodiments, sensor(s) 409 are included in an implantable housing of implantable medical device 410, attached to implantable medical device 410, coupled to implantable medical device 410 through wired or wireless connections, and/or incorporated into lead system 108. Implantable medical device 410 is a specific embodiment of implantable medical device 110 and includes cardiac pacing system 120 (including its various embodiments) and an implant telemetry circuit 450.

External system 415 includes an external telemetry circuit 452, an ischemia alert signal receiver 454, and a user interface 456. External telemetry circuit 452 and implant telemetry circuit 450 supports telemetry link 112, through which directional communication is performed between external system 415 and implantable system 405. User interface 456 includes a presentation device 458 and a user input device 460. Presentation device 458 includes a display screen. In one embodiment, presentation device 458 further includes a printer and a speaker. User input device 460 allows programming of implantable medical device 410, including the entry of commands for initiating one or more cardiac protection pacing sequences and/or parameters controlling the delivery of the cardiac protection pacing therapy. In one embodiment, portions of presentation device 458 and user input device 460 are integrated as an interactive screen. Ischemia alert signal receiver 454 receives the ischemia alert signal produced by ischemia detector 224 and transmitted to external system 415 via telemetry link 112 and, in response, causes presentation device 458 to produce an alarm signal and/or a warning message for the patient and/or a physician or caregiver.

In one embodiment, external system 415 includes a programmer. In another embodiment, external system 415 includes a patient management system as discussed below with reference to FIG. 5.

Figure 5:
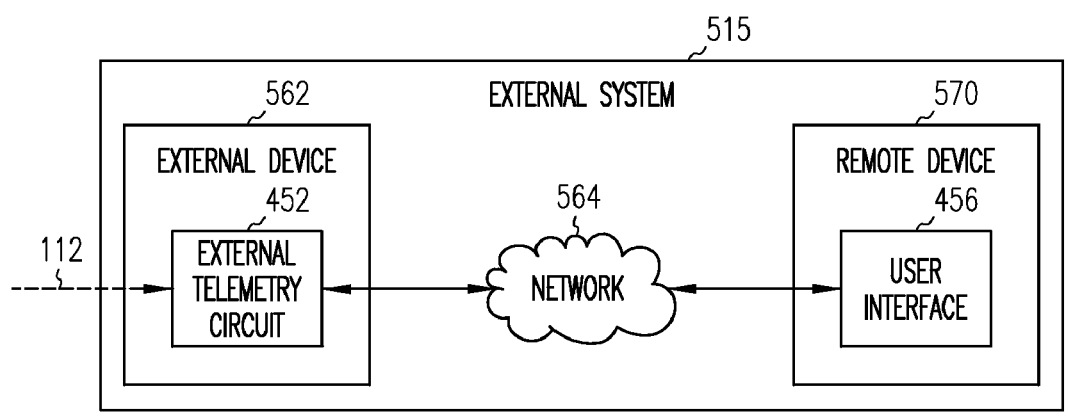
FIG. 5 is a block diagram illustrating an embodiment of the external system.

FIG. 5 is a block diagram illustrating an embodiment of an external system 515, which is a specific embodiment of external system 415. As illustrated in FIG. 5, external system 415 is a patient management system including an external device 562, a telecommunication network 564, and a remote device 570. External device 562 is placed within the vicinity of an implantable medical device and includes external telemetry system 452 to communicate with the implantable medical device via telemetry link 112. Remote device 570 is in one or more remote locations and communicates with external device 562 through network 564, thus allowing a physician or other caregiver to monitor and treat a patient from a distant location and/or allowing access to various treatment resources from the one or more remote locations. In one embodiment, as illustrated in FIG. 5, remote device 570 includes user interface 456. This allows the user to initiate and/or adjust the cardiac protection pacing therapy in response to the alarm signal and/or warning message associated with the ischemia alert signal.

Figure 6:
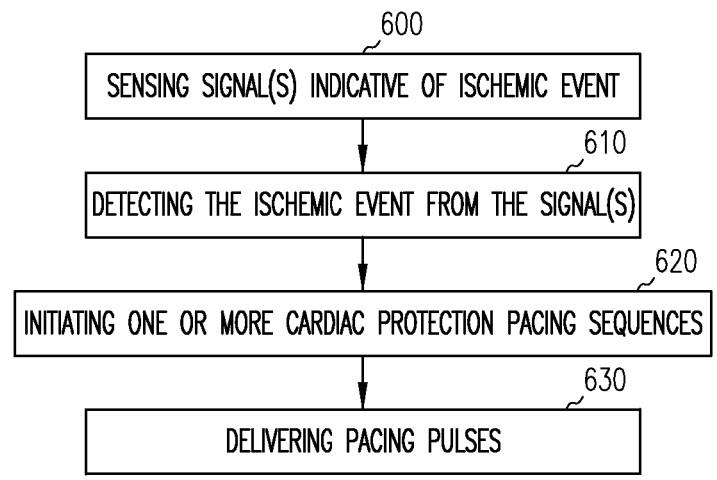
FIG. 6 is a flow chart illustrating an embodiment of a method for delivering pacing pulses for cardiac protection.

FIG. 6 is a flow chart illustrating an embodiment of a method for delivering pacing pulses for cardiac protection against tissue damage associated with ischemic events. In one embodiment, the method is performed by system 100.

One or more signals indicative of an ischemic event are sensed at 600. The ischemic event is detected from the one or more signals at 610. In response to the detection of the ischemic event, one or more cardiac protection pacing sequences are initiated at 620. The one or more cardiac protection pacing sequences each include alternating pacing and non-pacing periods. The pacing periods each have a pacing duration during which a plurality of pacing pulses is delivered. The non-pacing periods each having a non-pacing duration during which no pacing pulse is delivered. The plurality of pacing pulses is delivered during each of the pacing periods at 630.

Figure 7:
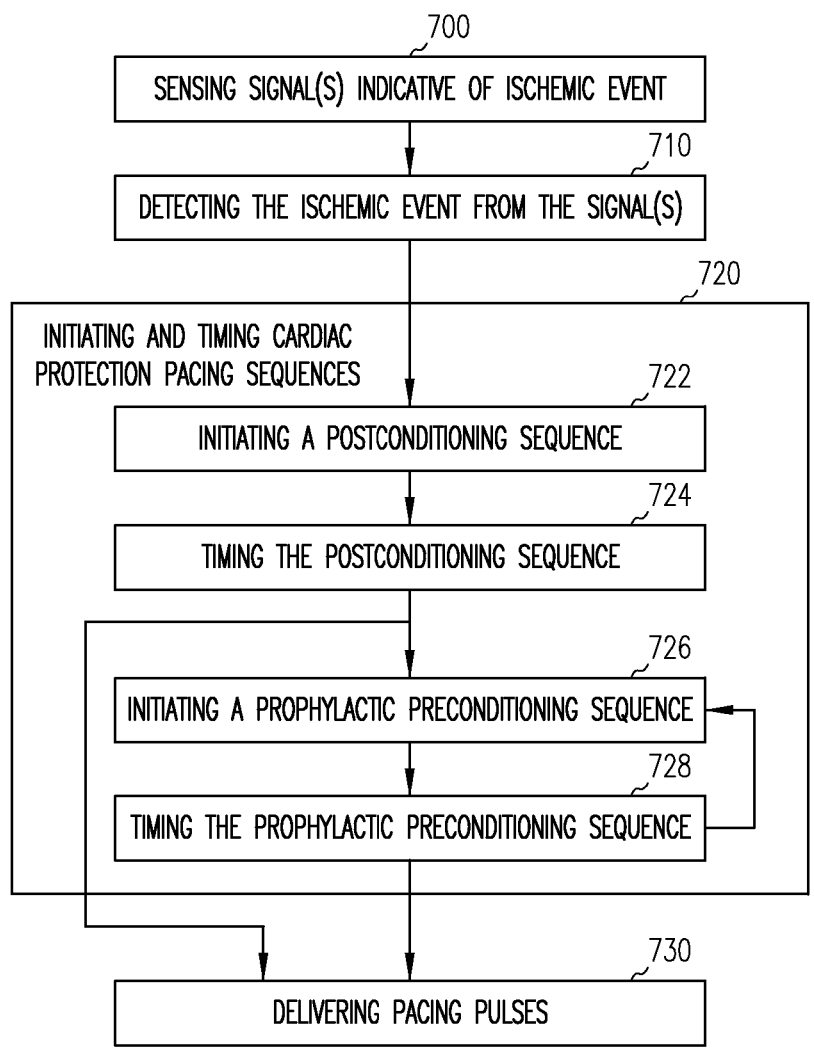
FIG. 7 is a flow chart illustrating a specific embodiment of the method for delivering pacing pulses for cardiac protection.

FIG. 7 is a flow chart illustrating a specific embodiment of the method for delivering pacing pulses for cardiac protection that is discussed with reference to FIG. 6. In one embodiment, the method is performed by system 100.

One or more signals indicative of an ischemic event are sensed at 700. The one or more signals are selected from surface ECG signals or other surface biopotential signals indicative of cardiac activities, wireless ECG signals, electrogram signals, impedance signals, heart sound signals, pressure signals, acceleration signals, signals representative of HRV parameters, and/or any other signals having characteristics allowing detection of ischemic events.

The ischemic event is detected from the one or more signals at 710, by running an automatic ischemia detection algorithm. In one embodiment, an ischemia alert signal is produced to indicate the detection of the ischemic event to the patient and/or a physician or other caregiver.

In response to the detection of the ischemic event, cardiac protection pacing sequences are initiated and timed at 720. In one embodiment, a pacing mode is switched from a chronic pacing mode to a temporary pacing mode when a cardiac protection pacing sequence is initiated and switched back from the temporary pacing mode to the chronic pacing mode when the cardiac protection pacing sequence is completed. The pacing mode determines whether and how pacing pulses are delivered before, during, and after the cardiac protection pacing sequence. To trigger the heart's intrinsic protective mechanism against tissue damage associated with ischemia, the temporary pacing mode is substantially different from the chronic pacing mode. In one embodiment, one or more cardiac protection pacing sequences are also initiated in response to user commands.

The cardiac protection pacing sequences include at least one postconditioning sequence and a plurality of prophylactic preconditioning sequences. In response to the detection of the ischemic event, postconditioning sequence is initiated at 722. In one embodiment, the postconditioning sequence is initiated when the end of the ischemic event is detected. In a specific embodiment, the end of the ischemic event is detected when the ischemic event is no longer detected. In a specific embodiment, the postconditioning pacing sequence is initiated when a post-ischemia time interval expires. The post-ischemia time interval starts at the end of the ischemic event and ends after a predicted reperfusion period following the ischemic event has started. In another embodiment, the postconditioning sequence is initiated in response to a post-conditioning command issued by a user. After being initiated, the postconditioning sequence including alternating postconditioning pacing and non-pacing periods is timed at 724. The postconditioning pacing periods each have a postconditioning pacing duration during which a plurality of pacing pulses is delivered. The postconditioning non-pacing periods each have a postconditioning non-pacing duration during which no pacing pulse is delivered. After the postconditioning sequence is completed, the prophylactic preconditioning sequences are initiated, one at a time, at 726. In one embodiment, the prophylactic preconditioning pacing sequences are initiated on a periodic basis with a predetermined period. In another embodiment, the prophylactic preconditioning pacing sequences are initiated according to a preconditioning schedule programmed by the user. In another embodiment, the prophylactic preconditioning pacing sequences are initiated in response to one or more preconditioning commands issued by the user. After being initiated, each of the prophylactic preconditioning pacing sequences including alternating preconditioning pacing and non-pacing periods is timed at 728. The preconditioning pacing periods each have a preconditioning pacing duration during which a plurality of pacing pulses is delivered. The preconditioning non-pacing periods each have a preconditioning non-pacing duration during which no pacing pulse is delivered. In one embodiment, predetermined type arrhythmias are detected. The one or more cardiac protection pacing sequences are suspended in response to the detection of the arrhythmia.

The plurality of pacing pulses is delivered during each of the pacing periods of the cardiac protection pacing sequences at 730. That includes the delivery of pacing pulses during the postconditioning pacing periods of the postconditioning sequence and the delivery of pacing pulses during the preconditioning pacing periods of each of the preconditioning sequences.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method for delivering pacing pulses, the method comprising:
   sensing one or more signals indicative of an ischemic event;
   detecting the ischemic event from the one or more signals;
   initiating one or more cardiac protection pacing sequences in response to the detection of the ischemic event, the one or more cardiac protection pacing sequences each including alternating pacing and non-pacing, periods, the pacing periods each having a pacing duration during which a plurality of pacing pulses is delivered, the nm-pacing periods each having a non-pacing duration during which no pacing pulse is delivered; and
   delivering the plurality of pacing pulses during each of the pacing periods.

2. The method of claim 1, further comprising switching a pacing mode from a chronic pacing mode to a temporary pacing mode when one of the one or more cardiac protection pacing sequence is initiated and to switch the pacing mode from the temporary pacing mode to the chronic pacing mode when the one of the one or more cardiac protection pacing sequence is completed, the temporary pacing mode substantially different from the chronic pacing mode.

3. The method of claim 1, wherein the one or more cardiac protection pacing sequences comprises at least one postconditioning sequence, and further comprising initiating the at least one postconditioning sequence after an end of the ischemic event is detected.

4. The method of claim 3, wherein initiating the at least one postconditioning sequence comprises initiating the at least one postconditioning pacing sequence when a post-ischemia time interval expires, the post-ischemia time interval starting when the end of the ischemic event is detected and is up to approximately 10 minutes.

5. The method of claim 3, further comprising timing the at least one postconditioning sequence having a postconditioning sequence duration in a range of approximately 30 seconds to 1 hour and including alternating postconditioning pacing and non-pacing periods, the postconditioning pacing periods each having a postconditioning pacing duration in a range of approximately 5 seconds to 10 minutes during which the plurality of pacing pulses is delivered, the postconditioning non-pacing periods each having a postconditioning non-pacing duration in a range of approximately 5 seconds to 10 minutes during which no pacing pulse is delivered.

6. The method of claim 5, wherein the one or more cardiac protection pacing sequences further comprise a plurality of prophylactic preconditioning sequences, and further comprising initiating the prophylactic preconditioning sequences after the postconditioning sequence is completed.

7. The method of claim 6, wherein initiating the prophylactic preconditioning sequences comprises initiating the prophylactic preconditioning pacing sequences on a periodic basis using a predetermined period in a range of approximately 24 hours to 72 hours.

8. The method of claim 6, wherein initiating the prophylactic preconditioning sequences comprises initiating the prophylactic preconditioning pacing sequences in response to one or more preconditioning commands.

9. The method of claim 6, further comprising timing the plurality of prophylactic preconditioning pacing sequences each having a preconditioning sequence duration in a range of approximately 10 minutes to 1 hour and each including alternating preconditioning pacing and non-pacing periods, the preconditioning pacing periods each having a preconditioning pacing duration in a range of approximately 1 minute to 30 minutes during which the plurality of pacing pulses is delivered, the preconditioning non-pacing periods each having a preconditioning non-pacing duration in a range of approximately 1 minute to 30 minutes during which no pacing pulse is delivered.

10. The method of claim 1, further comprising:
detecting an arrhythmia; and
suspending the one or more cardiac protection pacing sequences when the arrhythmia is detected.

11. The method of claim 1, wherein sensing the one or more signals comprises sensing one or more cardiac signals, and detecting the ischemic event comprises detecting the ischemic event from the one or more cardiac signals.

12. The method of claim 11, wherein sensing the one or more cardiac signals comprises sensing surface biopotentials using multiple surface electrodes.

13. The method of claim 11, wherein sensing the one or more cardiac signals comprises sensing one or more subcutaneous electrocardiogram signals using subcutaneously implantable electrodes.

14. The method of claim 11, wherein sensing the one or more cardiac signals comprises sensing one or more electrogram signals using implantable endocardial or epicardial electrodes.

15. The method of claim 1, wherein sensing the one or more signals comprises sensing an impedance signal indicative of a cardiac impedance or transthoracic impedance, and detecting the ischemic event comprises detecting the ischemic event from the impedance signal.

16. The method of claim 1, wherein sensing the one or more signals comprises sensing a signal indicative of heart sounds, and detecting the ischemic event comprises detecting the ischemic event from the signal indicative of heart sounds.

17. The method of claim 1, wherein sensing the one or more signals comprises sensing a pressure signal indicative of a blood pressure, and detecting the ischemic event comprises detecting the ischemic event from the pressure signal.

18. The method of claim 1, wherein sensing the one or more signals comprises sensing an acceleration signal indicative of regional cardiac wall motion, and detecting the ischemic event comprises detecting the ischemic event from the acceleration signal.

19. The method of claim 1, wherein sensing the one or more signals comprises sensing a heart rate variability (HRV) signal indicative of an HRV parameter, and detecting the ischemic event comprises detecting the ischemic event from the HRV signal.

20. A method for operating an implantable medical device, the method comprising:
sensing one or more signals indicative of an ischemic event using the implantable medical device;
detecting the ischemic event from the one or more signals using the implantable medical device;
initiating one or more cardiac protection pacing sequences in response to the detection of the ischemic event using the implantable medical device, the one or more cardiac protection pacing sequences each including alternating pacing and non-pacing periods, the pacing periods each having a pacing duration during which a plurality of pacing pulses is delivered, the non-pacing periods each having a non-pacing duration during which no pacing pulse is delivered; and
delivering the plurality of pacing pulses from the implantable medical device during each of the pacing periods.

* * * * *